United States Defensive Publication [19] (H) [11] T997,004

Leone [43] Aug. 5, 1980

[54] ACYLHYDRAZINOPHENYLTHIOUREA NUCLEATING AGENTS AND PHOTOGRAPHIC EMULSIONS AND ELEMENTS CONTAINING SUCH AGENTS

[76] Inventor: Ronald E. Leone, c/o Kodak Park Division, Rochester, N.Y. 14650

[21] Appl. No.: 105,317

[22] Filed: Dec. 19, 1979

Related U.S. Application Data

[62] Division of Ser. No. 56,588, Jul. 11, 1979, abandoned.

[51] Int. Cl.[3] ..... G03C 5/24; C07C 121/60; C07C 157/09; C07D 207/24

[52] U.S. Cl. ..... 430/378; 430/598; 260/465 D; 260/552 R; 260/326.4; 546/225

[57] ABSTRACT

Novel 3,3-disubstituted acylhydrazinophenylthiourea nucleating agents are disclosed as well as silver halide photographic emulsions and elements containing silver halide grains capable of forming an internal latent image having the nucleating agents adsorbed to the surface of the silver halide grains. Imaging processes in which these materials participate are also disclosed.

15 Claims, No Sheets Drawing,

78 Pages Specification

The file of this unexamined application may be inspected and copies thereof may be purchased (849 O.G. 1221, Apr. 9, 1968).